United States Patent [19]

Lunkenheimer et al.

[11] 4,284,791

[45] Aug. 18, 1981

[54] COMBATING FUNGI WITH N-CHLOROACETYL-N-(2,6-DI-SUBSTITUTED PHENYL)-ALANINE ESTERS

[75] Inventors: Winfried Lunkenheimer, Wuppertal; Wilhelm Brandes; Peter Kraus, both of Cologne, all of Fed. Rep. of Germany

[73] Assignee: Bayer Aktiengesellschaft, Leverkusen, Fed. Rep. of Germany

[21] Appl. No.: 839,716

[22] Filed: Oct. 5, 1977

[30] Foreign Application Priority Data

Oct. 23, 1976 [DE] Fed. Rep. of Germany ....... 2648074

[51] Int. Cl.³ .................... C07C 101/44; A61K 31/215
[52] U.S. Cl. ........................................ 560/43; 424/309
[58] Field of Search ........................... 424/309; 560/43

[56] References Cited

U.S. PATENT DOCUMENTS

| 3,598,859 | 8/1971 | Yates et al. | 560/43 |
| 3,712,805 | 1/1973 | Yates et al. | 71/111 |
| 3,763,216 | 10/1973 | Bertrand | 560/43 |
| 3,780,090 | 12/1973 | Akiba et al. | 71/111 |
| 3,830,829 | 8/1974 | Olin | 560/43 |
| 4,025,648 | 5/1977 | Hybele | 424/309 |
| 4,032,657 | 6/1977 | Moser | 560/43 |

Primary Examiner—G. T. Breitenstein
Attorney, Agent, or Firm—Sprung, Felfe, Horn, Lynch & Kramer

[57] ABSTRACT

N-Chloroacetyl-N-(2,6-di-substituted phenyl)-alanine esters of the formula

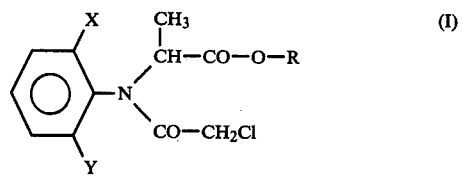

in which
R represents alkyl with 3 or more carbon atoms, alkenyl, alkynyl, halogenoalkyl, cycloalkyl, cycloalkylalkyl, alkoxyalkyl, alkoxyalkoxyalkyl, alkylthioalkyl, alkylsulphinylalkyl, alkylsulphonylalkyl, acyloxyalkyl, dialkylaminoalkyl or optionally substituted arylalkyl,
X represents alkyl or halogen, and
Y represents alkyl,
which possess fungicidal properties.

1 Claim, No Drawings

COMBATING FUNGI WITH N-CHLOROACETYL-N-(2,6-DI-SUBSTITUTED PHENYL)-ALANINE ESTERS

The present invention relates to and has for its objects the provision of particular new N-chloroacetyl-N-(2,6-di-substituted phenyl)-alanine esters which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has been disclosed in Phytopathology 33, 1,113 (1963) that zinc ethylene-1,2-bis-dithiocarbamate is a good agent for combating fungal diseases of plants. However, it is possible to use this compound only to a restricted extent since it is not very effective in certain ranges of indications, especially when low amounts and concentrations are used.

The present invention now provides, as new compounds, the N-chloroacetyl-N-phenyl-alanine esters of the general formula

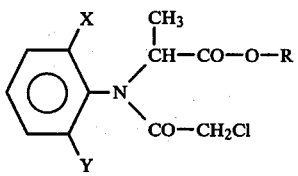

(I)

in which

R represents alkyl with 3 or more carbon atoms, alkenyl, alkynyl, halogenoalkyl, cycloalkyl, cycloalkylalkyl, alkoxyalkyl, alkoxyalkoxyalkyl, alkylthioalkyl, alkylsulphinylalkyl, alkylsulphonylalkyl, acyloxyalkyl, dialkylaminoalkyl or optionally substituted arylalkyl, X represents alkyl or halogen, and Y represents alkyl.

Preferably, R represents straight-chain or branched alkyl with 3 to 6 carbon atoms, alkenyl with 2 to 4 carbon atoms, alkynyl with 2 to 4 carbon atoms, halogenoalkyl with 1 to 4 carbon atoms and up to 5 halogen atoms (especially with up to 2 carbon atoms and up to 3 identical or different halogen atoms, the halogens being preferably fluorine or chlorine), cycloalkyl with 3 to 7 carbon atoms, cycloalkylalkyl with 3 to 7 carbon atoms in the cycloalkyl part and 1 to 4 carbon atoms in the alkyl part, alkoxyalkyl, alkoxyalkoxyalkyl, alkylthioalkyl, alkylsulphinylalkyl, alkylsulphonylalkyl or dialkylaminoalkyl, each with 1 to 4 carbon atoms in each alkyl part, or acyloxyalkyl with 1 to 4 carbon atoms in the alkyl part, the radical R' in the acyl part, which has the general formula R'—CO—, denoting alkyl with 1 to 4 carbon atoms, halogenoalkyl with 1 to 4 carbon atoms and up to 5 halogen atoms (especially with up to 2 carbon atoms and up to 3 identical or different halogen atoms, the halogens being preferably fluorine or chlorine), aryl with 6 to 10 carbon atoms (e.g. phenyl) or arylalkyl with 6 to 10 carbon atoms in the aryl part and 1 to 4 carbon atoms in the alkyl part (e.g. benzyl), the said aryl radicals optionally being substituted by halogen (especially fluorine, chlorine or bromine), cyano, nitro, alkyl with 1 or 2 carbon atoms or halogenoalkyl with up to 2 carbon atoms and up to 3 identical or different halogen atoms (the halogens being preferably fluorine or chlorine, as in trifluoromethyl, for example), or R represents arylalkyl which has 6 to 10 carbon atoms in the aryl part (preferably phenyl) and 1 to 4 carbon atoms in the alkyl part and is optionally substituted in the aryl part by halogen, (especially fluorine, chlorine or bromine), cyano, nitro, alkyl with 1 to 2 carbon atoms and halogenoalkyl with up to 2 carbon atoms and up to 3 identical or different halogen atoms (the halogens being preferably fluorine or chlorine, as in trifluoromethyl, for example);

X represents alkyl with 1 to 4 carbon atoms, chlorine or bromine; and

Y represents alkyl with 1 to 4 carbon atoms.

Those compounds of the formula (I), in which X and Y each represent methyl and R represents alkoxyalkyl with up to 2 carbon atoms in each alkyl part or represents alkenyl or alkynyl, each with up to 4 carbon atoms, exhibit a particularly good activity.

Surprisingly, the N-chloroacetyl-N-phenyl-alanine esters according to the invention exhibit a substantially better fungicidal activity, especially against Phytophthora, than zinc ethylene-1,2-bis-dithiocarbamate, which is known from the state of the art. The active compounds according to the invention thus represent an enrichment of the art.

The present invention also provides a process for the preparation of an N-chloroacetyl-N-phenyl-alanine ester of the formula (I), in which an N-phenyl-alanine ester of the general formula

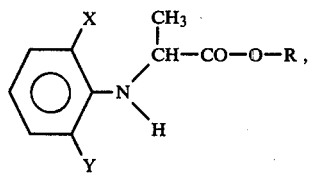

(II)

in which R, X and Y have the meanings stated above, is reacted with a chloroacetylating agent in the presence of a solvent and, if appropriate, in the presence of an acid-binding agent.

If N-(2,6-dimethylphenyl)-alanine 2-methoxyethyl ester and chloroacetyl chloride are used as the starting materials, the course of the reaction can be represented by the following equation:

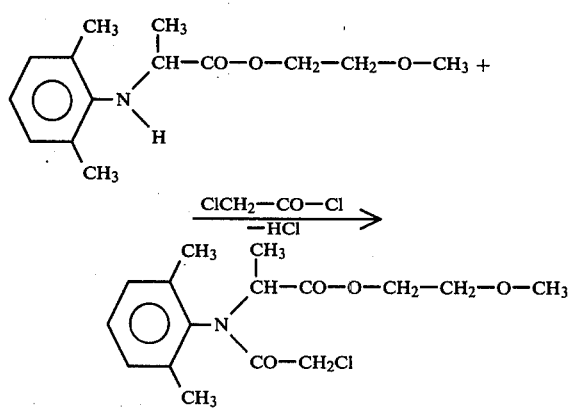

The N-phenyl-alanine esters of the formula (II) have not previously been described in the literature. They can be obtained in a simple manner by, for example, saponifying N-phenyl-alanine methyl esters of the general formula

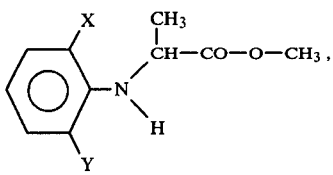

in which X and Y have the meanings stated above, in the customary manner and subsequently reacting the product according to known processes with the corresponding alcohols in the presence of boron trifluoride (see Synthetic Communications 4 (1974) 167–181 and also the preparative examples hereinbelow).

However, the N-phenyl-alanine methyl esters of the formula (III) can also be converted direct to the N-phenyl-alanine esters of the formula (II) in a known manner (see the preparative examples).

The N-phenyl-alanine methyl esters of the formula (III) are either known from inter alia, German Offenlegungsschriften (German Published Specifications) Nos. 2,350,944 and 2,513,730, and they can be obtained easily by processes indicated in these specifications, by reacting the corresponding anilines with α-halogenopropionic acid methyl esters.

Examples of the starting materials of the formula (II) which may be mentioned are: N-(2,6-dimethylphenyl)-alanine n-butyl ester, N-(2,6-dimethylphenyl)-alanine cyclohexylmethyl ester, N-(2,6-dimethylphenyl)-alanine cyclopropylmethyl ester, N-(2,6-dimethylphenyl)-alanine 2-methylthioethyl ester, N-(2,6-dimethylphenyl)-alanine 2-methylsulphinylethyl ester, N-(2,6-dimethylphenyl)-alanine 2-methylsulphonylethyl ester, N-(2,6-dimethylphenyl)-alanine 2-dimethylaminoethyl ester, N-(2,6-dimethylphenyl)-alanine benzyl ester, N-(2,6-dimethylphenyl)-alanine, 2,4-dichlorobenzyl ester, N-(2,6-dimethylphenyl)-alanine 2-(2-methoxyethoxy)-ethyl ester, N-(2-ethyl-6-methylphenyl)-alanine n-butyl ester, N-(2-ethyl-6-methylphenyl)-alanine cyclohexylmethyl ester, N-(2-ethyl-6-methylphenyl)-alanine cyclopropylmethyl ester, N-(2-ethyl-6-methylphenyl)-alanine 2-methylthioethyl ester, N-(2-ethyl-6-methylphenyl)-alanine 2-methylsulphinylethyl ester, N-(2-ethyl-6-methylphenyl)-alanine 2-methylsulphonylethyl ester, N-(2-ethyl-6-methylphenyl)-alanine 2-dimethylaminoethyl ester, N-(2-ethyl-6-methylphenyl)-alanine benzyl ester, N-(2-ethyl-6-methylphenyl)-alanine 2,4-dichlorobenzyl ester, N-(2-ethyl-6-methylphenyl)-alanine 2-(2-methoxyethoxy)-ethyl ester, N-(2-ethyl-6-methylphenyl)-alanine i-propyl ester, N-(2-ethyl-6-methylphenyl)-alanine n-propyl ester, N-(2-ethyl-6-methylphenyl)-alanine 2-chloroethyl ester, N-(2-ethyl-6-methylphenyl)-alanine 2-methoxyethyl ester, N-(2-ethyl-6-methylphenyl)-alanine allyl ester, N-(2-ethyl-6-methylphenyl)-alanine propargyl ester, N-(2-ethyl-6-methylphenyl)-alanine cyclohexyl ester, N-(2-ethyl-6methylphenyl)-alanine 2-ethoxyethyl ester, N-(2-ethyl-6-methylphenyl)-alanine 2-chloroacetoxyethyl ester, N-(2-chloro-6-methylphenyl)-alanine n-butyl ester, N-(2-chloro-6-methylphenyl)-alanine cyclohexylmethyl ester, N-(2-chloro-6-methylphenyl)-alanine cyclopropylmethyl ester, N-(2-chloro-6-methylphenyl)-alanine 2-methylthioethyl ester, N-(2-chloro-6-methylphenyl)-alanine 2-methylsulphinylethyl ester, N-(2-chloro-6-methylphenyl)-alanine 2-methylsulphonylethyl ester, N-(2-chloro-6-methylphenyl)-alanine 2-dimethylaminoethyl ester, N-(2-chloro-6-methylphenyl)-alanine benzyl ester, N-(2-chloro-6-methylphenyl)-alanine 2,4-dichlorobenzyl ester, N-(2-chloro-6-methylphenyl)-alanine 2-(2-methoxyethoxy)-ethyl ester, N-(2-chloro-6-methylphenyl)-alanine i-propyl ester, N-(2-chloro-6-methylphenyl)-alanine n-propyl ester, N-(2-chloro-6-methylphenyl)-alanine 2-chloroethyl ester, N-(2-chloro-6-methylphenyl)-alanine 2-methoxyethyl ester, N-(2-chloro-6-methylphenyl)-alanine allyl ester, N-(2-chloro-6-methylphenyl)-alanine propargyl ester, N-(2-chloro-6-methylphenyl)-alanine cyclohexyl ester, N-(2-chloro-6-methylphenyl)-alanine 2-ethoxyethyl ester, N-(2-chloro-6-methylphenyl)-alanine 2-chloroacetoxyethyl ester, N-(2-chloro-6-ethylphenyl)-alanine n-butyl ester, N-(2-chloro-6-ethylphenyl)-alanine cyclohexylmethyl ester, N-(2-chloro-6-ethylphenyl)-alanine cyclopropylmethyl ester, N-(2-chloro-6-ethylphenyl)-alanine 2-methylthioethyl ester, N-(2-chloro-6-ethylphenyl)-alanine 2-methylsulphinyl ester, N-(2-chloro-6-ethylphenyl)-alanine 2-methylsulphonylethyl ester, N-(2-chloro-6-ethylphenyl)-alanine 2-dimethylaminoethyl ester, N-(2-chloro-6-ethylphenyl)-alanine benzyl ester, N-(2-chloro-6-ethylphenyl)-alanine 2,4-dichlorobenzyl ester, N-(2-chloro-6-ethylphenyl)-alanine 2-(2-methoxyethoxy)-ethyl ester, N-(2-chloro-6-ethylphenyl)-alanine i-propyl ester, N-(2-chloro-6-ethylphenyl)-alanine n-propyl ester, N-(2-chloro-6-ethylphenyl)-alanine 2-chloroethyl ester, N-(2-chloro-6-ethylphenyl)-alanine 2-methoxyethyl ester, N-(2-chloro-6-ethylphenyl)-alanine allyl ester, N-(2-chloro-6-ethylphenyl)-alanine propargyl ester, N-(2-chloro-6-ethylphenyl)-alanine cyclohexyl ester, N-(2-chloro-6-ethylphenyl)-alanine 2-ethoxyethyl ester, N-(2-chloro-6-ethylphenyl)-alanine 2-chloroacetoxyethyl ester, N-(2,6-diethylphenyl)-alanine n-butyl ester, N-(2,6-diethylphenyl)-alanine cyclohexylmethyl ester, N-(2,6-diethylphenyl)-alanine cyclopropylmethyl ester, N-(2,6-diethylphenyl)-alanine 2-methylthioethyl ester, N-(2,6-diethylphenyl)-alanine 2-methylsulphinylethyl ester, N-(2,6-diethylphenyl)-alanine 2-methylsulphonylethyl ester, N-(2,6-diethylphenyl)-alanine 2-dimethylaminoethyl ester, N-(2,6-diethylphenyl)-alanine benzyl ester, N-(2,6-diethylphenyl)-alanine 2,4-dichlorobenzyl ester, N-(2,6-diethylphenyl)-alanine 2-(2-methoxyethoxy)-ethyl ester, N-(2,6-diethylphenyl)-alanine i-propyl ester, N-(2,6-diethylphenyl)-alanine n-propyl ester, N-(2,6-diethylphenyl)-alanine 2-chloroethyl ester, N-(2,6-diethylphenyl)-alanine 2-methoxyethyl ester, N-(2,6-diethylphenyl)-alanine allyl ester, N-(2,6-diethylphenyl)-alanine propargyl ester, N-(2,6-diethylphenyl)-alanine cyclohexyl ester, N-(2,6-diethylphenyl)-alanine 2-ethoxyethyl ester and N-(2,6-diethylphenyl)-alanine 2-chloroacetoxyethyl ester.

Preferred chloroacetylating agents which can be used for the reaction according to the invention are chloroacetyl chloride and chloroacetic acid anhydride.

Preferred solvents which can be used for the reaction according to the invention are inert organic solvents, especially ketones, such as diethyl ketone and in particular acetone and methyl ethyl ketone; nitriles, such as propionitrile and especially acetonitrile; ethers, such as tetrahydrofuran or dioxane; aliphatic and aromatic hydrocarbons, such as petroleum ether, benzene, toluene or xylene; halogenated hydrocarbons, such as methylene chloride, carbon tetrachloride, chloroform or chlorobenzene; and esters, such as ethyl acetate.

The process according to the invention can, if appropriate, be carried out in the presence of an acid-binding agent (hydrogen chloride acceptor); acid-binding agents which can be used are all the customary acid acceptors. These include organic bases, preferably tertiary amines, such as, for example, triethylamine; and also inorganic bases, such as, for example, alkali metal hydroxides and alkali metal carbonates.

When carrying out the process according to the invention, the reaction temperatures can be varied within a substantial range. In general, the reaction is carried out at from 0° to 120° C. and preferably at from 20° to 100° C.

In carrying out the process according to the invention, 1 to 1.5 moles of the chloroacetylating agent and 1 to 1.5 moles of the acid-binding agent are preferably employed per mole of the compound of the formula (II). The compounds of the formula (I) are isolated in a customary manner.

It is also possible to obtain a pure optical antipode of a compound of the formula (I) by, in a first stage, reacting an N-phenyl-alanine of the general formula

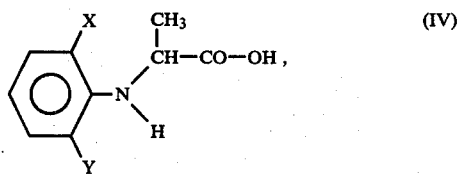

in which X and Y have the meanings stated above, [which is formed as an intermediate during the preparation of the starting material of the formula (II)] in a known manner with a N-containing, optically active base, such as, for example, phenylethylamine, brucine or quinine, in the presence of a diluent and separating the resulting diastereomeric salts on the basis of their differing solubilities; then, in a second stage, liberating the optical antipode of the acid of the formula (IV) from the corresponding salt with the aid of a strong acid, such as, for example, hydrochloric acid or sulphuric acid, if appropriate in the presence of a solvent; then, in a third stage, reacting the free optical antipode of the acid of the formula (IV) with the corresponding alcohol to give the optically active ester of the formula (II); and, in the fourth stage, carrying out the halogeno-acetylation, in accordance with the process of the invention.

Examples which may be mentioned of particularly active representatives of the active compounds according to the invention are, in addition to the compounds in the preparative examples, the chloroacetylated compounds derived from the starting materials of the formula (II) which have already been mentioned as examples.

The active compounds according to the invention exhibit a powerful fungitoxic action and bacteriotoxic action. They do not damage crop plants in the concentrations required for combating fungi and bacteria. For these reasons, they are suitable for use as plant protection agents for combating fungi and bacteria. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens.

They display a particularly good activity against parasitic fungi on above-ground parts of plants; thus, for example, good effects are achieved against the pathogen of late blight of tomato (*Phytophthora infestans*) and against the rice disease caused by the fungus *Pyricularia oryzae*. It is to be emphasized particularly that the active compounds according to the invention not only display a protective active but are also curatively active, that is to say when used after infection has taken place. The systemic action of the compounds is noteworthy. Thus, it proves possible to protect plants against fungal attack if the active compound is supplied to the above-ground parts of the plant through the soil and the root.

As plant protection agents, the compounds according to the invention can be used for the treatment of soil, for the treatment of seed and for the treatment of above-ground parts of plants.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as dichlorodifluoromethane and trichlorofluoromethane; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl ar polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant-protection agents, such as other fungicides, or insecticides, acaricides, nematocides, bactericides, rodenticides, herbicides, fertilizers, growth-regulating agents, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

Especially when used as leaf fungicides, the active compound concentrations in the use forms can be varied within a fairly wide range. They are, in general, from 0.00001 to 0.1 percent by weight, preferably from 0.0001 to 0.05 percent.

When higher amounts and higher concentrations are used, the compounds according to the invention also exhibit a herbicidal action.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon the intended application. Therefore, in special cases it is possible to go above or below the aforementioned concentration ranges.

The process of the present invention is illustrated by the following preparative examples:

EXAMPLE 1

(a) Preparation of the starting material

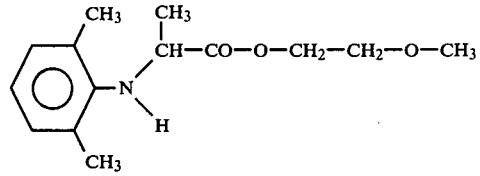

1,000 ml (2 mol) of 2 molar methanolic potassium hydroxide solution were added to a solution of 207 g (1 mol) of N-(2,6-dimethylphenyl)-alanine methyl ester in 1,000 ml of methanol and the mixture was heated under reflux for 3 hours. After cooling, the reaction solution was acidified with 190 ml of concentrated hydrochloric acid, the potassium chloride which had precipitated was filtered off and the filtrate was evaporated in vacuo. The oily residue crystallized on grinding and warming with 350 ml of ethyl acetate and 100 ml of petroleum ether. 133 g (68% of theory) of N-(2,6-dimethylphenyl)-alanine with a melting point of 178°–180° C. were obtained.

28.3 g (0.2 mol) of 48% strength boron trifluoride etherate were added dropwise to a suspension of 19.4 g (0.1 mol) of N-(2,6-dimethylphenyl)-alanine in 152 g (2 mol) of ethylene glycol monomethyl ether and the mixture was heated under reflux (100° C.) for 18 hours. The filtered reaction mixture was poured into 100 ml of 10% strength sodium carbonate solution. The oil which had separated out was then extracted with twice 100 ml of methylene chloride, the extract was dried over sodium sulphate and evaporated and the residue was fractionated in vacuo. This gave 15 g (60% of theory) of N-(2,6-dimethylphenyl)-alanine 2-methoxyethyl ester with a boiling point of 141°–144° C./0.7 mm Hg.

(b) The starting material could also be obtained by the following route:

25.5 g (0.18 mol) of 48% strength boron trifluoride etherate were added to a solution of 18.6 g (0.09 mol) of N-(2,6-dimethylphenyl)-alanine methyl ester in 273 g (3.6 mol) of ethylene glycol monomethyl ether and the mixture was heated under reflux (100° C.) for 23 hours. The reaction solution was poured into 200 ml of 10% strength sodium carbonate solution. The oil which had separated out was then extracted with methylene chloride, the extract was dried over sodium sulphate and evaporated and the residue was fractionated in vacuo. This gave 14.6 g (65% of theory) of N-(2,6-dimethylphenyl)-alanine 2-methoxyethyl ester with a boiling point of 142°-147° C./0.7 mm Hg.

(c)

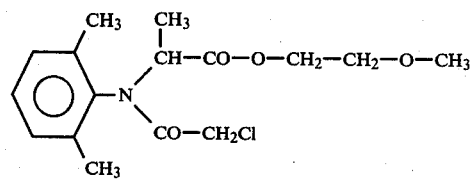

10.5 g (0.093 mol) of chloroacetyl chloride were added dropwise at 30° to 35° C., in the course of 20 minutes, to a mixture of 19.4 g (0.0774 mol) of N-(2,6-dimethylphenyl)-alanine 2-methoxyethyl ester, 9.8 g (0.093 mol) of sodium carbonate and 150 ml of toluene and the mixture was stirred for a further 20 hours at room temperature. The reaction mixture was filtered, the filtrate was evaporated, the residue was dissolved in 150 ml of ethyl acetate and the solution was washed with half-concentrated hydrochloric acid and water, dried over sodium sulphate and evaporated. This gave 19.3 g (76% of theory) of N-chloroacetyl-N-(2,6-dimethylphenyl)-alanine 2-methoxyethyl ester in the form of a viscous oil ($n_D^{22}=1.5196$).Fp. 70°-71° C. (Ligroin).

EXAMPLE 2

(a) Preparation of the starting material

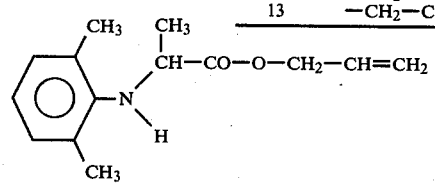

70.8 g (0.5 mol) of 48% strength boron trifluoride etherate were added to a solution of 48.5 g (0.25 mol) of N-(2,6-dimethylphenyl)-alanine in 290 g (5 mols) of allyl alcohol and the mixture was heated under reflux for 4 hours. After cooling, the reaction solution was filtered and poured into 750 ml of 10% strength sodium carbonate solution. The oil which had separated out was extracted with methylene chloride, the extract was dried over sodium sulphate and evaporated and the residue was fractionated in vacuo. This gave 24.7 g (42.2% of theory) of N-(2,6-dimethylphenyl)-alanine allyl ester with a boiling point of 118°-122° C./1 mm Hg.

(b)

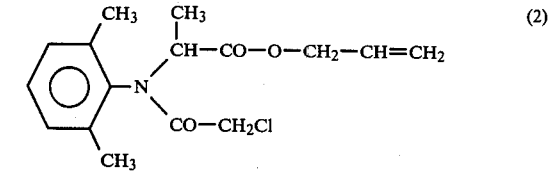

13.6 g (0.12 mol) of chloroacetyl chloride were added dropwise at 30° to 35° C., in the course of 20 minutes, to a mixture of 23.3 g (0.1 mol) of N-(2,6-dimethylphenyl)-alanine allyl ester, 12.7 g (0.12 mol) of sodium carbonate and 190 ml of toluene and the mixture was stirred for a further 24 hours at room temperature. The reaction mixture was filtered, the filtrate was evaporated, the residue was dissolved in 150 ml of ethyl acetate and the solution was washed with half-concentrated hydrochloric acid and water, dried over sodium sulphate and evaporated. This gave 23.1 g (75% of theory) of N-chloroacetyl-N-(2,6-dimethylphenyl)-alanine allyl ester in the form of a viscous oil which on prolonged standing solidified to a crystalline mass with a melting point of 55°-56° C.

The compounds in Table 1 which follows were obtained analogously:

TABLE 1

(I)

| Compound No. | R | X | Y | Physical constants |
|---|---|---|---|---|
| 3 | i-C$_3$H$_7$ | CH$_3$ | CH$_3$ | $n_D^{24}$:1.5128 |
| 4 | —CH$_2$—CH$_2$—Cl | CH$_3$ | CH$_3$ | Melting point:74–74.5° C. |
| 5 | n-C$_3$H$_7$ | CH$_3$ | CH$_3$ | $n_D^{24}$:1.5155 |
| 6 | —CH$_2$—C≡CH | CH$_3$ | CH$_3$ | Melting point:84–85° C. |
| 7 | ⟨H⟩ | CH$_3$ | CH$_3$ | $n_D^{24}$:1.5215 |
| 8 | —CH$_2$—CH$_2$—OC$_2$H$_5$ | CH$_3$ | CH$_3$ | $n_D^{24}$:1.5149 |
| 9 | —CH$_2$—CH$_2$—O—CO—CH$_2$Cl | CH$_3$ | CH$_3$ | Melting point:69–71° C. |
| 10 | —CH$_2$—CH$_2$—O—CH$_2$—CH$_2$—O—CH$_3$ | CH$_3$ | CH$_3$ | $n_D^{24}$ = 1.5125 |
| 11 | —CH$_2$—CH$_2$—O—CH$_3$ | CH$_3$ | C$_2$H$_5$ | $n_D^{22,5}$ = 1.5206 |
| 12 | —CH$_2$—CH$_2$—O—CH$_3$ | C$_2$H$_5$ | C$_2$H$_5$ | $n_D^{23}$ = 1.5160 |
| 13 | —CH$_2$—CH$_2$—O—CH$_3$ | i-C$_3$H$_7$ | i-C$_3$H$_7$ | $n_D^{24}$ = 1.5080 |

The fungicidal activity of the compounds of this invention is illustrated by the following biotest examples in which the compounds according to the present invention are each identified by the number (given in brackets) from the preparative examples hereinabove.

The known comparison compound A has the formula:

$$(A) = \begin{array}{c} \phantom{CH_2-NH-}\overset{S}{\underset{\|}{C}}\phantom{-S} \\ CH_2-NH-C-S \\ | \phantom{CH_2-NH-C-}\diagdown \\ \phantom{CH_2-NH-C-S}Zn \\ | \phantom{CH_2-NH-C-}\diagup \\ CH_2-NH-C-S \\ \underset{\|}{\phantom{CH_2-NH-}}\underset{S}{\phantom{C}} \end{array}$$

EXAMPLE 3

Phytophthora test (tomato)/systemic
Solvent: 4.7 parts by weight of acetone
Emulsifier: 0.3 part by weight of alkylaryl polyglycol ether
Water: 95 parts by weight The amount of active compound required for the desired concentration of the active compound in the watering liquid was mixed with the stated amount of solvent and the concentrate was diluted with the stated amount of water which contained the stated amount of the emulsifier.

Tomato plants grown in standard soil and having 2 to 4 foliage leaves were watered three times in the course of one week with 10 ml of the watering liquid, having the stated concentration of active compound, per 100 ml of soil.

The plants treated in this way were inoculated, after the treatment, with an aqueous spore suspension of *Phytophthora infestans*. The plants were brought into a humidity chamber at an atmospheric humidity of 100% and a temperature of 18° to 20° C. After 5 days, the infection of the tomato plants was determined. The assessment data obtained were converted to percent infection. 0% denoted no infection and 100% denoted that the plants were totally infected.

The active compounds, the concentrations of the active compound and the results can be seen from the following table:

TABLE 2

| | Phytophthora test / systemic |
|---|---|
| Active compound | Infection in % at an active compound concentration of 100 ppm |
| (A) | 90 |
| (1) | 0 |
| (2) | 5 |
| (6) | 0 |

EXAMPLE 4

Phytophthora test (tomato)/curative
Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated amount of emulsifier.

Young tomato plants with 2 to 4 foliage leaves were inoculated with an aqueous spore suspension of *Phytophthora infestans*. The plants remained for 7 hours at 20° C. and a relative atmospheric humidity of 100%.

After a short drying-off time, the plants were sprayed with the spray liquid, prepared in the manner described above, until dripping wet, and were then brought into a moist chamber at 100% atmospheric humidity and 18° to 20° C.

After 5 days the infection of the tomato plants was determined. The assessment data were converted to percent infection: 0% meant no infection; 100% meant that the plants were totally infected.

The active compounds, the concentrations of the active compound and the results can be seen from the following table:

TABLE 3

| | Phytophthora test / curative |
|---|---|
| Active compound | Infection in % at an active compound concentration of 0.025% |
| (A) | 62 |
| (1) | 26 |
| (2) | 11 |
| (6) | 20 |

EXAMPLE 5

Phytophthora test (tomato)/protective
Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C. and at a relative atmospheric humidity of 70%. The tomato plants were then inoculated with an aqueous spore suspension of *Phytophthora infestans*. The plants were brought into a moist chamber with an atmospheric humidity of 100% and a temperature of 18°–20° C.

After 5 days the infection of the tomato plants was determined. The assessment data were converted to percent infection: 0% meant no infection; 100% meant that the plants were totally infected.

The active compounds, the concentrations of the active compound and the results can be seen from the following table:

TABLE 4

| | Phytophthora test / protective | |
|---|---|---|
| | Infection in % at an active compound concentration of | |
| Active compound | 0.001% | 0.0005% |
| (A) | 30 | 59 |
| (1) | — | 1 |
| (2) | 10 | 34 |
| (6) | — | 9 |

EXAMPLE 6

Pyricularia test/rice/systemic
Solvent: 11.75 parts by weight of acetone
Dispersing agent: 0.75 part by weight of alkylaryl polyglycol ether
Water: 987.50 parts by weight The amount of active compound required for the desired concentration of active compound in the watering liquid was mixed with the stated amount of the solvent and dispersing agent and the concentrate was diluted with the stated amount of water.

The amount it was desired to use of the liquor thus obtained was placed in saucers on which stood pots, with perforated bottoms, containing 30 rice plants which were about 2 weeks old. The test preparations were taken up through the root.

After 3 days, during which the plants remained in a greenhouse at 22° to 24° C. and about 70% relative atmospheric humidity, the plants were inoculated with an aqueous suspension of 100,000 to 200,000 spores/ml of *Pyricularia oryzae* and were set up in a room at 24° to 26° C. and 100% relative atmospheric humidity.

About 4 days after the inoculation, the infection of all leaves present at the time of the inoculation was determined in comparison with the untreated, but also inoculated, control plants.

The evaluation is made in terms of a scale of 1–9. 1 meant a 100% action, 3 denoted a good action, 5 denoted a moderate action and 9 denoted no action.

The active compounds, the amounts used and the results can be seen from the table which follows:

TABLE 5

| Pyricularia test / rice / systemic | | |
|---|---|---|
| Active compound | Amount used | Infection rating |
| (A) | 10 kg/ha | 9 |
| (2) | 10 kg/ha | 3 |
| (6) | 10 kg/ha | 2 |

It will be appreciated that the instant specification and examples are set forth by way of illustration and not limitation, and that various modifications and changes may be made without departing from the spirit and scope of the present invention.

What is claimed is:

1. N-chloroacetyl-N-(2,6-dimethylphenyl)-alanine 2-methoxyethyl ester of the formula

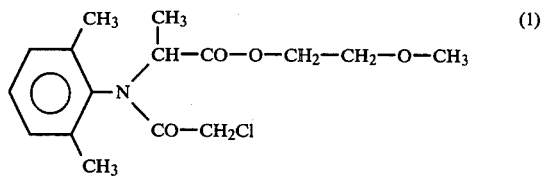

* * * * *